(12) United States Patent
Lin et al.

(10) Patent No.: US 10,470,787 B2
(45) Date of Patent: Nov. 12, 2019

(54) ROTARY SHAVER WITH AN ELECTROCAUTERY HEMOSTASIS FUNCTION

(71) Applicant: KAOHSIUNG MEDICAL UNIVERSITY, Kaohsiung (TW)

(72) Inventors: Yu-Chuan Lin, Kaohsiung (TW); Pei-His Chou, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 336 days.

(21) Appl. No.: 15/649,254

(22) Filed: Jul. 13, 2017

(65) Prior Publication Data

US 2019/0015126 A1  Jan. 17, 2019

(51) Int. Cl.
*A61B 17/32* (2006.01)
*A61B 17/3205* (2006.01)
*A61B 18/14* (2006.01)
*A61B 18/00* (2006.01)
*A61B 18/12* (2006.01)

(52) U.S. Cl.
CPC .... *A61B 17/32002* (2013.01); *A61B 17/3205* (2013.01); *A61B 18/1206* (2013.01); *A61B 18/1445* (2013.01); *A61B 18/1482* (2013.01); *A61B 2018/00184* (2013.01); *A61B 2018/00202* (2013.01); *A61B 2018/00595* (2013.01)

(58) Field of Classification Search
CPC .......... A61B 17/32002; A61B 17/3205; A61B 18/1206; A61B 18/1445; A61B 18/1482; A61B 2018/00184; A61B 2018/00202; A61B 2018/00595
See application file for complete search history.

(56) References Cited

U.S. PATENT DOCUMENTS

| | | | |
|---|---|---|---|
| 5,364,395 A * | 11/1994 | West, Jr. | A61B 17/32002 604/22 |
| 7,674,263 B2 * | 3/2010 | Ryan | A61B 18/148 606/180 |
| 9,078,664 B2 * | 7/2015 | Palmer | A61B 18/148 |
| 9,901,394 B2 * | 2/2018 | Shadduck | A61B 18/148 |
| 10,188,456 B2 * | 1/2019 | Prisco | A61B 18/1485 |
| 10,314,647 B2 * | 6/2019 | Bloom | A61B 18/148 |

* cited by examiner

*Primary Examiner* — Michael F Peffley

(57) ABSTRACT

A rotary shaver for tissue resection includes an elongated outer tubular member, an elongated inner cutting member disposed in and operatively rotatable relative to the outer tubular member for cutting a tissue, and an elongated jaw member disposed in the outer tubular member to surround the inner cutting member and operatively turnable to cooperate with an outer distal portion of the outer tubular member so as to clamp and electrocauterize the tissue for creating hemostasis during a surgical procedure.

8 Claims, 6 Drawing Sheets

ROTARY SHAVER WITH AN ELECTROCAUTERY HEMOSTASIS FUNCTION

FIELD

The disclosure relates to a rotary surgical instrument for endoscopic tissue resection, and more particularly to a rotary shaver with an electrocautery hemostasis function.

BACKGROUND

Minimally invasive surgeries using arthroscopy have been vigorously developed in recent years for minimizing the size of incisions needed and so lessening wound healing time, associated pain and risk of infection. During an arthroscopic surgical procedure performed on a shoulder joint or hip joint of a patient, electrocautery is needed for establishing hemostasis. Often, an elongated electrocautery tool, such as that disclosed in Taiwanese Patent No. 1571234, is separated from an elongated arthroscopic cutter for tissue resection and is used to cauterize but not to cut the tissue. After cutting the tissue, the arthroscopic cutter is removed to be replaced with the electrocautery tool at the surgical site, which is cumbersome to the surgeon. The surgeon needs to take much time to find the bleeder in the bleeding area, thus increasing the surgical time and risk.

A manner to dispense with instrument exchange is making an additional incision for introducing the electrocautery tool. However, in such manner, not only the incision increment results in the risk of infection and increase of the healing time, but also use of the electrocautery tool still after removal of the arthroscopic cutter is time-consuming.

SUMMARY

Therefore, an object of the disclosure is to provide a rotary shaver with an electrocautery hemostasis function that can alleviate at least one of the drawbacks of the prior art.

According to the disclosure, the rotary shaver for resecting a tissue includes an elongated outer tubular member defining a first lumen therein, an elongated inner cutting member disposed in the first lumen and operatively rotatable relative to the outer tubular member, and an elongated jaw member disposed in the first lumen and between the outer tubular member and the inner cutting member. The outer tubular member includes an outer cylindrical portion and an outer distal portion which extends in an elongated direction from the outer cylindrical portion and which has a first notch opening that is in communication with the first lumen. The inner cutting member defines a second lumen therein, and includes an inner cylindrical portion and an inner distal portion which extends in the elongated direction from the inner cylindrical portion to be disposed in the outer distal portion. The inner distal portion has a second notch opening in communication with the second lumen and the first notch opening and bordered by a cutting edge. The jaw member is operatively turnable relative to the outer tubular member to a clamping position, where the jaw member cooperates with the outer distal portion to clamp a portion of the tissue that is inserted into the second notch opening through the first notch opening. The outer tubular member and the jaw member are configured to allow an electric current to pass therethrough so as to generate heat applied to the tissue for electrocautery when the jaw member is in the clamping position, while the inner cutting member is rotated relative to the outer tubular member for cutting the clamped tissue in the second notch opening.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
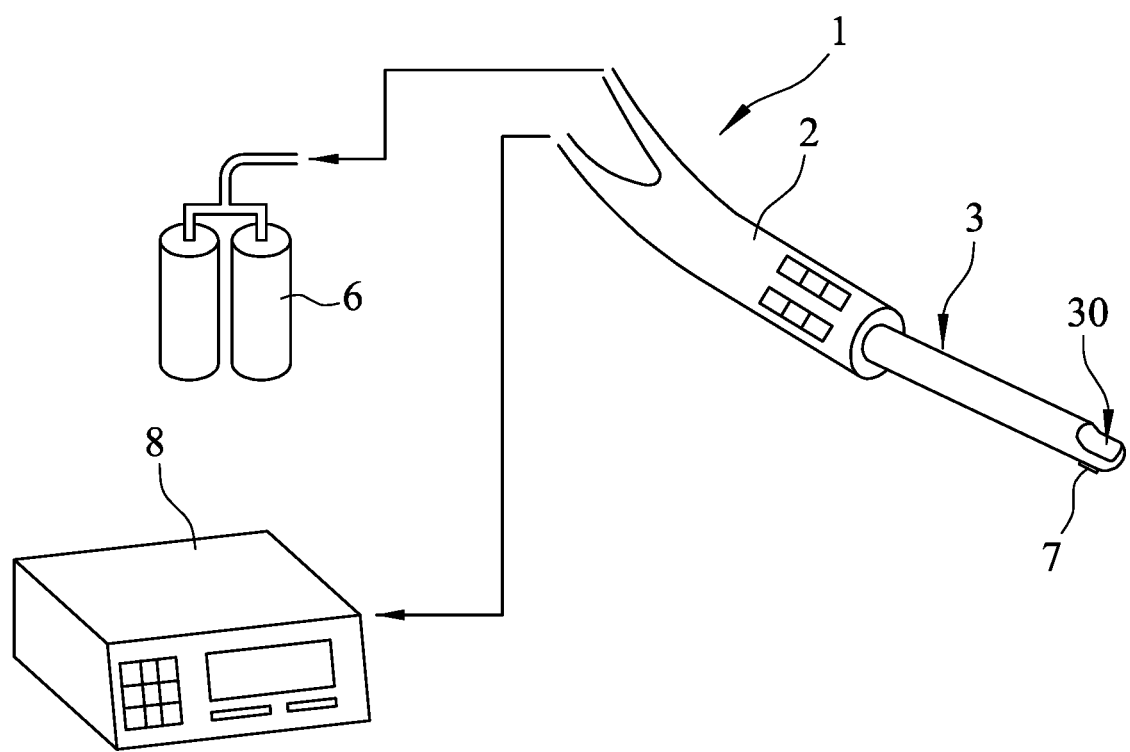
FIG. 1 is a schematic view illustrating an embodiment of a rotary shaver according to the disclosure.
Figure 2:
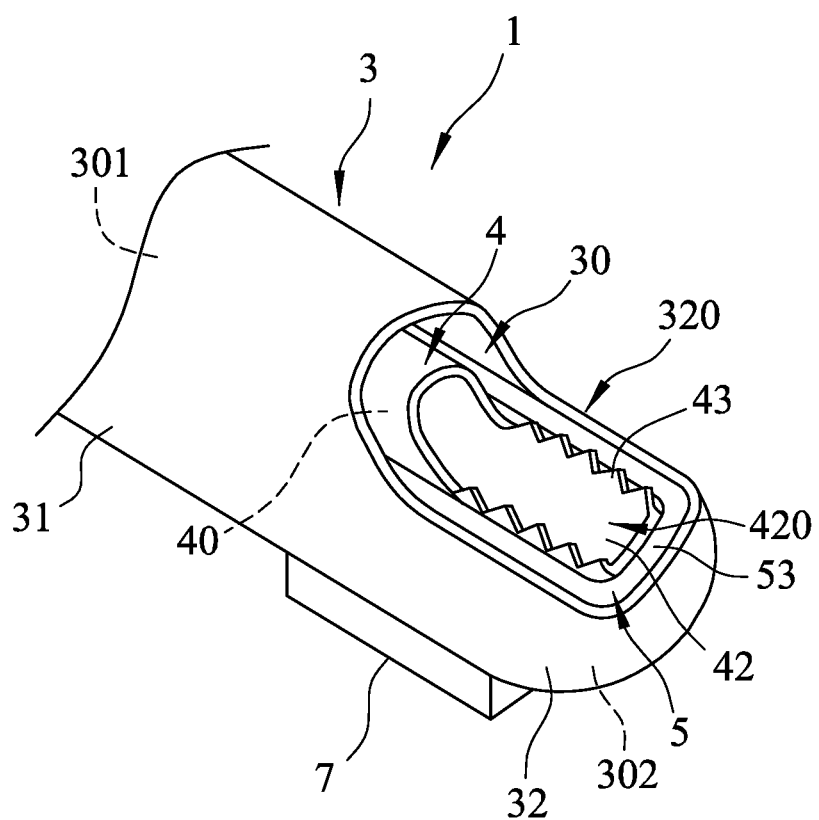
FIG. 2 is a fragmentary, perspective view of the embodiment.

Referring to FIGS. 1 and 2, an embodiment of a rotary shaver 1 according to the disclosure includes a driving controller 2, an elongated outer tubular member 3 connected with the driving controller 2 and defining a first lumen 30 therein, an elongated inner cutting member 4 connected with the driving controller 2, disposed in the first lumen 30 and defining a second lumen 40 therein, an elongated jaw member 5 connected with the driving controller 2 and disposed in the first lumen 30 and between the outer tubular member 3 and the inner cutting member 4, an aspirator 6 connected with the driving controller 2 and in communication with the second lumen 40 of the inner cutting member 4, and an auxiliary electrocautery member 7 disposed on the outer tubular member 3 and outwardly of the first lumen 30. In this embodiment, the driving controller 2 is of a transmitting construction which has a clutch means for individually driving rotation of the inner cutting member 4 and turning of the jaw member 5 relative to the outer tubular member 3, and serves as a power supply to the aspirator 6 for generating a negative pressure. Since the construction of the driving controller 2 is of a known type, a description thereof is dispensed with herein.

Figure 3:
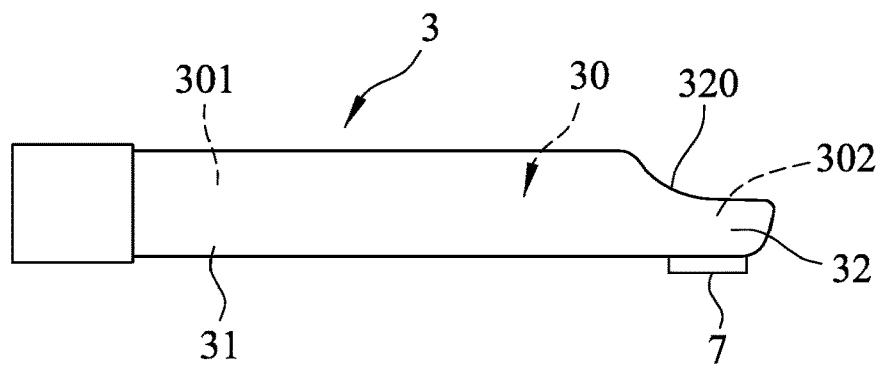
FIG. 3 is a schematic side view of an elongated outer tubular member of the embodiment.

Referring to FIGS. 1 to 3, the outer tubular member 3 includes an outer cylindrical portion 31 which is connected with the driving controller 2, and an outer distal portion 32 which extends in an elongated direction from the outer cylindrical portion 31 and which has a first notch opening 320. The first lumen 30 includes a lumen section 301 defined in the outer cylindrical portion 31, and a receiving section 302 defined in the outer distal portion 32 and in communication with the lumen section 301. The first notch opening 320 is in communication with the first lumen 30 to serve as an access thereof.

Figure 4:
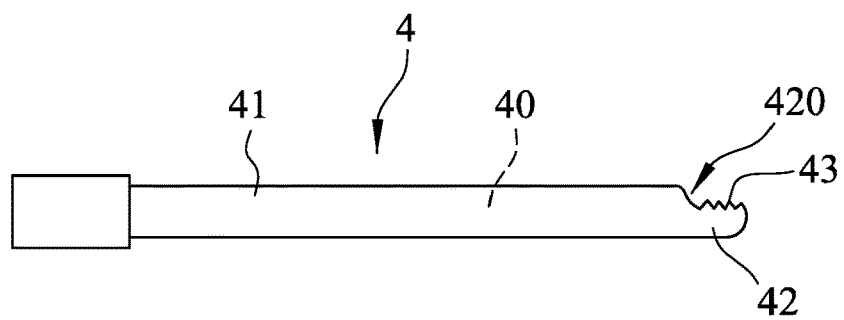
FIG. 4 is a schematic side view of an elongated inner cutting member of the embodiment.

Referring to FIGS. 1, 2 and 4, the inner cutting member 4 includes an inner cylindrical portion 41 which is connected with the driving controller 2 and which is disposed in the lumen section 301, and an inner distal portion 42 which extends in the elongated direction from the inner cylindrical portion 41 to be disposed in the receiving section 302. The inner distal portion 42 has a second notch opening 420 which is in communication with the second lumen 40 and the first notch opening 320 and which is bordered by a cutting edge 43. The cutting edge 43 is in the form of serrations. The inner cutting member 4 is operatively rotatable relative to the outer tubular member 3 for cutting a tissue (B).

Figure 5:
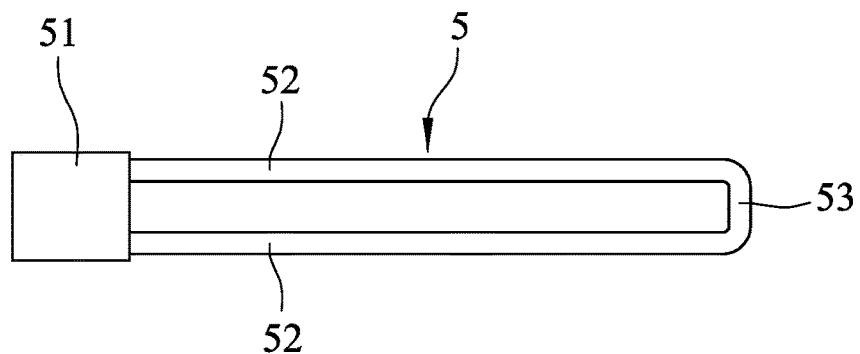
FIG. 5 is a schematic side view of an elongated jaw member of the embodiment.
Figure 6:
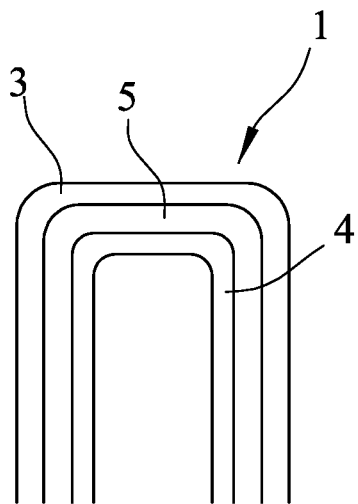
FIG. 6 is a schematic view illustrating the jaw member disposed between the outer tubular member and the inner cutting member.

Referring to FIGS. 2, 5 and 6, the jaw member 5 is disposed between the outer tubular member 3 and the inner cutting member 4, and includes a connecting socket 51 which is electrically connected with the driving controller 2 (see FIG. 1), two shaft portions 52 which are connected to the connecting socket 51 and are disposed respectively at two opposite sides of the inner cylindrical portion 41 (see FIG. 4) of the inner cutting member 4 and in the lumen section 301 and each of which extends in the elongated direction from the connecting socket 51, and a connecting portion 53 which is of a U-shape and which interconnects the shaft portions 52 to surround the inner distal portion 42 in the receiving section 302. The shaft portions 52 and the connecting portion 53 are interposed between the outer tubular member 3 and the inner cutting member 4 to surround the inner cutting member 4. It should be noted that the shaft portions 52 are disposed in the lumen section 301 and are not exposed to the first notch opening 320 while the connecting portion 53 is disposed in the receiving section 302 and is exposed to the first notch opening 320 (see FIG. 2).

Figure 7:
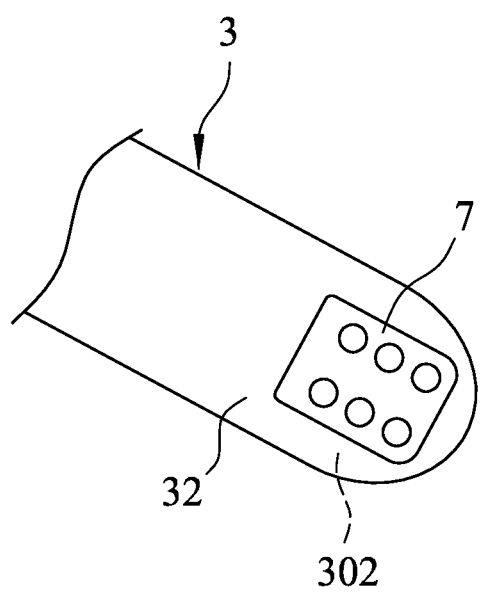
FIG. 7 is a fragmentary schematic view illustrating an auxiliary electrocautery member of the embodiment.

Referring to FIGS. 2 and 7, the auxiliary electrocautery member 7 is disposed on an outer surface of the outer distal portion 32 of the outer tubular member 3 and outwardly of the receiving section 302.

Figure 8:
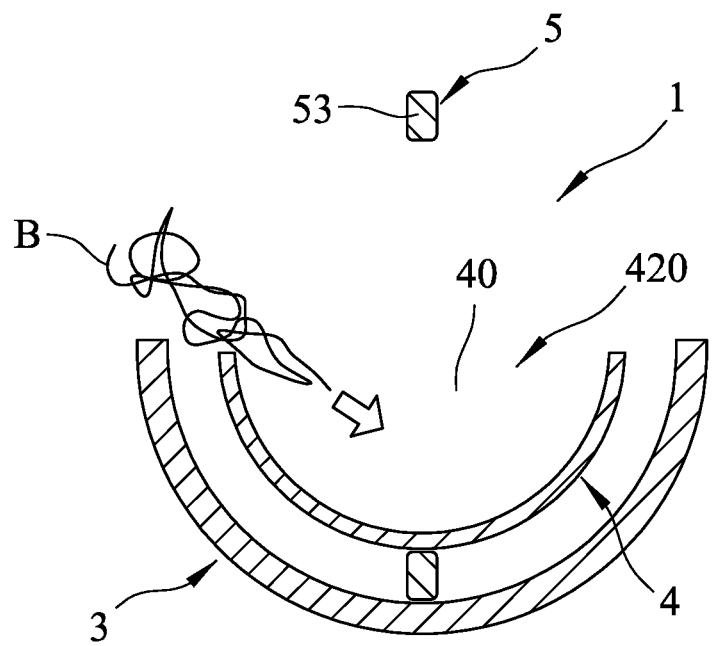
FIG. 8 is a schematic sectional view illustrating when a tissue is aspirated and partly inserted into a notch opening of the inner cutting member.
Figure 9:
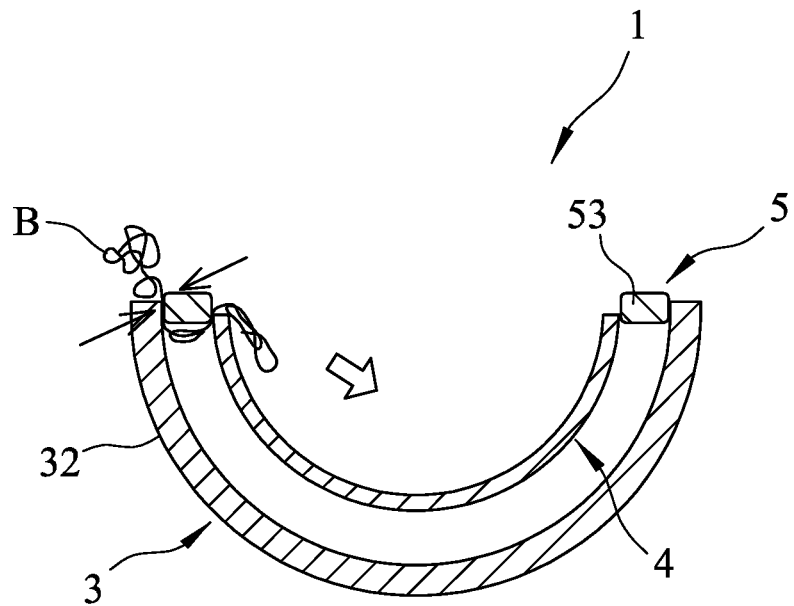
FIG. 9 is a schematic sectional view illustrating when the jaw member is turned to a clamping position to cooperate with the outer tubular member for clamping the tissue.

In operation, referring to FIGS. 1, 2 and 8, the driving controller 2 is operated to actuate the aspirator 6 to generate a negative pressure in the second lumen 40. The second notch opening 420 is brought near to the tissue (B) to be cut so as to draw the tissue (B) into the second notch opening 420 through the first notch opening 320, as shown in FIG. 8. With reference to FIG. 9, the driving controller 2 is subsequently operated to drive turning of the jaw member 5 relative to the outer tubular member 3 to a clamping position, where the connecting portion 53 of the jaw member 5 cooperates with the outer distal portion 32 of the outer tubular member 3 to clamp the tissue (B). It should be noted that, when the tissue (B) is inserted into the second notch opening 420 from a site as shown in FIG. 9, the jaw member 5 is turned in a counterclockwise direction to the clamping position. When the tissue (B) is inserted in an opposite direction, the jaw member 5 is turned in a clockwise direction to the clamping position.

Figure 10:
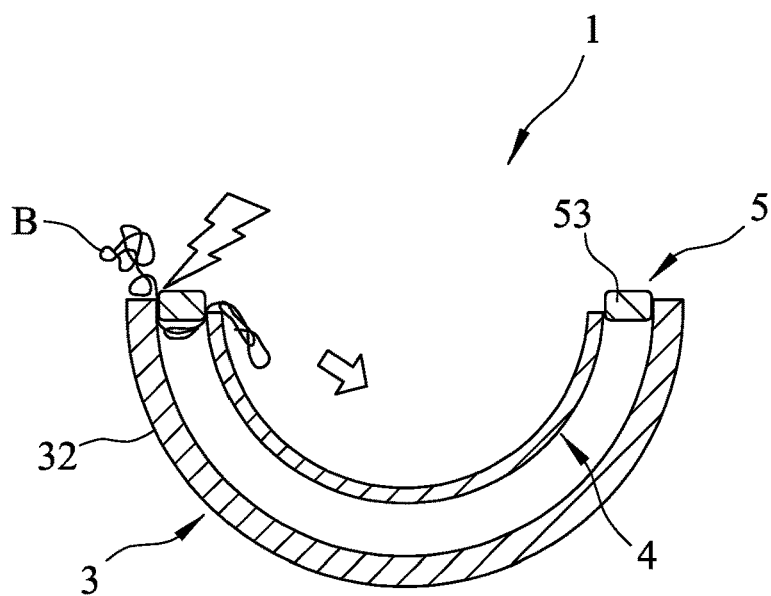
FIG. 10 is a schematic sectional view illustrating when an electric current passes through the jaw member and the outer tubular member to generate heat applied to the clamped tissue for electrocautery.
Figure 11:
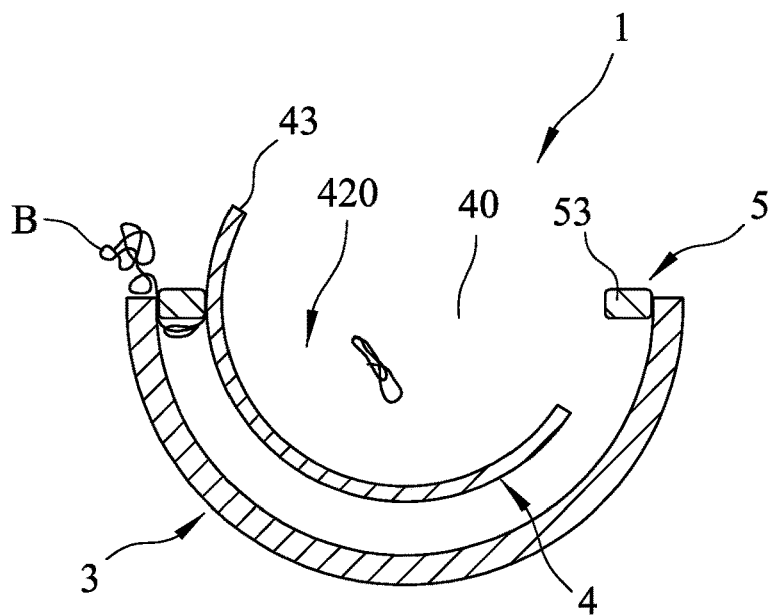
FIG. 11 is a schematic sectional view illustrating when the inner cutting member is rotated for cutting the clamped tissue.

Referring to FIG. 10, at this stage, the driving controller 2 is operated to allow an electric current to pass through the outer tubular member 3 and the jaw member 5 so as to generate heat on the outer distal portion 32 and the connecting portion 53 for electrocauterizing the clamped tissue (B). With reference to FIG. 11, after bleeding control, the driving controller 2 is operated to rotate the inner cutting member 4 relative to the outer tubular member 3 and the jaw member 5 for cutting the clamped tissue (B) in the second notch opening 420. The tissue debris is aspirated from the second notch opening 420 into the second lumen 40. As is apparent from the foregoing mentioned, the inner cutting member 4 is rotated in a clockwise direction to cut the tissue (B) (see FIG. 11). When the tissue (B) is clamped at an opposite site, the inner cutting member 4 is rotated in a counterclockwise direction. Moreover, the cut tissue (B), once bleeding, can be electrocauterized by the auxiliary electrocautery member 7.

The driving controller 2 may be connected with a computer device 8 as needed. The cutting edge 43 (see FIG. 2) may have another configuration other than the serrations as different requirements are to be met.

As illustrated, with the aspirator 6 which can draw the tissue (B) into the second notch opening 420 of the inner cutting member 4, with the outer distal portion 32 of the outer tubular member 3 which cooperates with the connecting portion 53 of the jaw member 5 to clamp firmly and electrocauterize the tissue (B) for creating hemostasis, and with the inner cutting member 4 rotatable for cutting the tissue (B), the electrocautery and resection procedures can be performed using a single rotary shaver. There is no need to remove an instrument from the operated site, and to insert another instrument and position the same at the operated point. The surgical time can be reduced and the surgical precision can be increased.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A rotary shaver for resecting a tissue, comprising:
    an elongated outer tubular member defining a first lumen therein, and including an outer cylindrical portion and an outer distal portion which extends in an elongated direction from said outer cylindrical portion and which has a first notch opening that is in communication with said first lumen;
    an elongated inner cutting member disposed in said first lumen and operatively rotatable relative to said outer tubular member, said inner cutting member defining a second lumen therein, and including an inner cylindrical portion and an inner distal portion which extends in the elongated direction from said inner cylindrical portion to be disposed in said outer distal portion, said inner distal portion having a second notch opening which is in communication with said second lumen and said first notch opening and which is bordered by a cutting edge; and
    an elongated jaw member disposed in said first lumen and between said outer tubular member and said inner cutting member, and operatively turnable relative to said outer tubular member to a clamping position, where said jaw member cooperates with said outer distal portion to clamp a portion of the tissue that is inserted into said second notch opening through said first notch opening;
    said outer tubular member and said jaw member being configured to allow an electric current to pass therethrough so as to generate heat applied to the tissue for electrocautery when said jaw member is in the clamping position, while said inner cutting member is rotated relative to said outer tubular member for cutting the clamped tissue in said second notch opening.

2. The rotary shaver as claimed in claim 1, wherein said jaw member includes two shaft portions respectively disposed at two opposite sides of said inner cutting member and each extending in the elongated direction, and a connecting portion which interconnecting said shaft portions, said shaft portions and said connecting portion being interposed between said outer tubular member and said inner cutting member to surround said inner cutting member.

3. The rotary shaver as claimed in claim 2, wherein said shaft portions are respectively disposed at two opposite sides of said inner cylindrical portion of said inner cutting member, and said connecting portion is of a U-shape and surrounds said inner distal portion of said inner cutting member such that said connecting portion cooperates with said outer distal portion of said outer tubular member to clamp and electrocauterize the tissue when said jaw member is in the clamping position.

4. The rotary shaver as claimed in claim 1, wherein said cutting edge is in the form of serrations.

5. The rotary shaver as claimed in claim 3, further comprising a driving controller which is connected with said outer tubular member, said inner cutting member and said jaw member to drive rotations of said inner cutting member and said jaw member, said jaw member further including a connecting socket which is connected to said shaft portions and electrically connected with said driving controller.

6. The rotary shaver as claimed in claim 1, further comprising an auxiliary electrocautery member which is disposed on and outwardly of said outer tubular member.

7. The rotary shaver as claimed in claim 6, wherein said auxiliary electrocautery member is disposed on and outwardly of an outer surface of said outer distal portion of said outer tubular member.

8. The rotary shaver as claimed in claim 1, further comprising an aspirator which is in communication with said second lumen of said inner cutting member to generate a negative pressure so as to aspirate the tissue from said second notch opening into said second lumen.

* * * * *